US010045859B2

(12) United States Patent
Butler et al.

(10) Patent No.: US 10,045,859 B2
(45) Date of Patent: Aug. 14, 2018

(54) CERVICAL AND LUMBAR SPINAL INTERBODY DEVICES

(71) Applicant: Life Spine, Inc., Huntley, IL (US)

(72) Inventors: Michael S. Butler, St. Charles, IL (US); Michael J. Milella, Jr., Huntley, IL (US)

(73) Assignee: Life Spine, Inc., Huntley, IL (US)

( * ) Notice: Subject to any disclaimer, the term of this patent is extended or adjusted under 35 U.S.C. 154(b) by 14 days.

(21) Appl. No.: 15/081,676

(22) Filed: Mar. 25, 2016

(65) Prior Publication Data

US 2016/0331543 A1    Nov. 17, 2016

Related U.S. Application Data

(63) Continuation of application No. 29/475,313, filed on Dec. 2, 2013, now Pat. No. Des. 753,305, which is a
(Continued)

(51) Int. Cl.
*A61F 2/44* (2006.01)
*A61F 2/30* (2006.01)
*A61F 2/46* (2006.01)

(52) U.S. Cl.
CPC ............ *A61F 2/447* (2013.01); *A61F 2/4465* (2013.01); *A61F 2/30771* (2013.01);
(Continued)

(58) Field of Classification Search
CPC ........... A61F 2/44; A61F 2/4455; A61F 2/446
See application file for complete search history.

(56) References Cited

U.S. PATENT DOCUMENTS

| 4,834,757 A | 5/1989 | Brantigan |
| 5,716,415 A | 2/1998 | Steffee |

(Continued)

FOREIGN PATENT DOCUMENTS

WO    WO-2008/033489 A3    3/2008

OTHER PUBLICATIONS

International Preliminary Report on Patentability for PCT/US2007/019974, dated Oct. 9, 2008, 6 pages.
(Continued)

*Primary Examiner* — David Bates
(74) *Attorney, Agent, or Firm* — Foley & Lardner LLP

(57) ABSTRACT

Lumbar and cervical interbody or intervertebral devices for implantation between adjacent vertebrae of a spine and/or within intermediary canals of long bones are characterized by a body defining a superior end and an inferior end whose surfaces have serrations or teeth thereon forming anti-backout structures that allow implantation of the body but inhibit removal or backing out therefrom. The one-way structures may extend from the anterior end to the posterior end. The one-way structures may take different shapes but are always configured to allow insertion of the interbody device in an anterior-first manner while preventing and/or inhibiting the interbody device from backing out posteriorly. The various interbody devices may be further characterized by a body defining a cavity that is in communication with the superior and inferior ends of the body and at least one lateral side thereof via openings in the body. Undercuts are formed in the body about the adjacent the openings in order to support bony ingrowth within the void.

18 Claims, 15 Drawing Sheets

Related U.S. Application Data continuation of application No. 11/900,944, filed on Sep. 14, 2007, now Pat. No. 8,597,359.

(60) Provisional application No. 60/844,561, filed on Sep. 14, 2006.

(52) U.S. Cl.
CPC ... *A61F 2/4611* (2013.01); *A61F 2002/30112* (2013.01); *A61F 2002/30593* (2013.01); *A61F 2002/30622* (2013.01); *A61F 2002/30784* (2013.01); *A61F 2002/30904* (2013.01); *A61F 2002/448* (2013.01); *A61F 2002/4475* (2013.01); *A61F 2230/0004* (2013.01)

(56) References Cited

U.S. PATENT DOCUMENTS

| | | | |
|---|---|---|---|
| 5,766,252 A | | 6/1998 | Henry et al. |
| 6,008,433 A | | 12/1999 | Stone |
| D444,878 S | | 7/2001 | Walter |
| D445,188 S | | 7/2001 | Walter |
| 6,468,311 B2 | * | 10/2002 | Boyd .................. A61F 2/28 623/17.11 |
| 6,482,233 B1 | * | 11/2002 | Aebi .................. A61F 2/4465 623/17.11 |
| 6,613,090 B2 | * | 9/2003 | Fuss .................. A61F 2/4455 623/17.11 |
| 6,823,871 B2 | | 11/2004 | Schmieding |
| 6,979,353 B2 | * | 12/2005 | Bresina .............. A61B 17/1637 623/17.11 |
| D524,443 S | | 7/2006 | Blain |
| D541,940 S | | 5/2007 | Blain |
| D611,147 S | | 3/2010 | Hanson et al. |
| D615,653 S | | 5/2010 | Horton |
| D623,748 S | | 9/2010 | Horton et al. |
| D623,749 S | | 9/2010 | Horton et al. |
| D627,468 S | | 11/2010 | Richter et al. |
| D631,967 S | | 2/2011 | Horton |
| 7,892,261 B2 | | 2/2011 | Bonutti |
| D650,481 S | | 12/2011 | Gottlieb et al. |
| D653,757 S | | 2/2012 | Binder |
| D674,900 S | | 1/2013 | Janice et al. |
| D677,791 S | | 3/2013 | Danacioglu et al. |
| D681,205 S | | 4/2013 | Farris et al. |
| 2002/0068976 A1 | | 6/2002 | Jackson |
| 2003/0105526 A1 | | 6/2003 | Bryant et al. |
| 2003/0139812 A1 | | 7/2003 | Garcia et al. |
| 2004/0082999 A1 | | 4/2004 | Mathys et al. |
| 2004/0254644 A1 | * | 12/2004 | Taylor .................. A61F 2/4425 623/17.13 |
| 2005/0131536 A1 | | 6/2005 | Eisermann et al. |
| 2005/0149193 A1 | | 7/2005 | Zucherman et al. |
| 2006/0015184 A1 | | 1/2006 | Winterbottom et al. |
| 2009/0182431 A1 | | 7/2009 | Butler et al. |
| 2012/0143334 A1 | | 6/2012 | Boyce et al. |
| 2013/0144389 A1 | | 6/2013 | Bonutti |

OTHER PUBLICATIONS

International Preliminary Report on Patentability for PCT/US2008/078038, dated Jul. 24, 2010, 5 pages.
International Search Report for PCT/US2008/078038, dated Nov. 25, 2008, 1 page.
Written Opinion for PCT/US2007/019974, dated Mar. 24, 2008, 6 pages.

\* cited by examiner

CERVICAL AND LUMBAR SPINAL INTERBODY DEVICES

CROSS-REFERENCE TO RELATED APPLICATIONS

This patent application is a continuation of U.S. patent application Ser. No. 29/475,313 filed on Dec. 2, 2013, which is a continuation of (and incorporated the disclosure of) U.S. patent application Ser. No. 11/900,944, which was filed on Sep. 14, 2007, which claims the benefit of and/or priority to (and incorporated the disclosure of) U.S. Provisional Patent Application No. 60/844,561 filed Sep. 14, 2006, the complete disclosure of which are hereby incorporated by reference herein.

BACKGROUND

Field

The present invention relates to interbody and/or cement restrictor devices for implantation between a pair of adjacent vertebrae in order to provide support to the vertebrae and/or promote bone fusion between the vertebrae or for implantation within the intermediary canals of a femur, tibia or humerus.

Background Information

The disc between vertebrae of a human spine is sometimes damaged due to disease or injury, or may simply deteriorate due to age, disease, injury or congenital defect. With others, the vertebrae may become compressed or otherwise damaged. In these and other cases the vertebrae can become too closely spaced anteriorly which causes an undesired abnormal curvature of the spine with respect to lordosis or kyphosis.

Because of this, surgery may be utilized to place one or more spacers or interbody devices between adjacent vertebrae to provide proper spacing of the vertebrae and which may also promote fusion between the vertebrae. When a device of this type is utilized for the purpose of promoting fusion, it is often termed a fusion cage or an intervertebral fusion device. When so utilized, bone or bone fusion material is often placed about or in the interbody device(s) in order to promote growth of the bone between the adjacent vertebrae.

Interbody devices known as cement restrictors may also be used in bones such as the femur, tibia or humerus for the same or similar reasons as vertebral interbody devices. In these cases, the interbody device is implanted within the intermediary canal of the particular bone.

When interbody devices are used, it is desirable for them to engage as much surface of the bone as possible to provide support to the bone and to thereby reduce the likelihood of subsidence of the device into the bone resulting from contact pressure of the interbody device against bone surfaces. Subsidence can occur since part of the bone is somewhat spongy in nature, especially near the centers of the adjacent vertebrae.

In summation, the structure of interbody devices mainly functions to support the two adjacent vertebral surfaces, unless the interbody device is also used as a fusion cage within or around which to pack bone fusion material, or to act as a cement restrictor within a long bone. Because it is also desirable in such structures to maintain weight and volume as low as possible in order to make the device more compatible with the body, it is also desirable to make the interbody device as small and lightweight as possible, while still maintaining strength.

Accordingly, there presently exists a need for improved interbody devices.

SUMMARY

The present invention provides lumbar and cervical interbody or intervertebral devices and/or long bone cement restrictor devices (collectively, interbody devices) for implantation between adjacent vertebrae of a spine and/or within intermediary canals of long bones such as the femur, tibia or humerus.

In accordance with an aspect of the present invention, the various interbody devices are characterized by a body defining a superior end and an inferior end whose surfaces have serrations or teeth thereon. These serrations or teeth allow easy implantation of the body but inhibit removal or backing out thereof after implantation and thus may be considered one-way structures. In one form, the one-way structures extend from an anterior end to a posterior end (i.e. one side to another of the body). The one-way structures may take different shapes but are always configured to allow insertion of the interbody device in an anterior-first manner while preventing and/or inhibiting the interbody device from backing out posteriorly.

In accordance with an aspect of the present invention, the various interbody devices are further characterized by a body defining an interior, cavity, void or the like that is in communication with the superior and inferior ends of the body and at least one lateral side thereof via a hole, bore, aperture, fissure, outlet, opening or the like. Undercuts are formed about the cavity adjacent the openings in the body in order to support bony ingrowth within the cavity. The undercuts may be configured in various manners depending on the overall configuration of the interbody device, the various voids formed in the interbody device and/or passages formed in the interbody device that provide communication between one or more interior voids and the exterior of the interbody device.

Various shapes of interbody devices are disclosed for various applications and/or various positions along the spine or long bone. The interbody devices also may include one or more bores on the posterior end of the body for aiding implantation. Some include markers on the upper and/or lower surfaces thereof.

BRIEF DESCRIPTION OF THE DRAWINGS

The above mentioned and other features, advantages and objects of this invention, and the manner of attaining them, will become apparent and the invention itself will be better understood by reference to the following description of embodiments of the invention taken in conjunction with the accompanying drawings, wherein.

Like reference numerals indicate the same or similar parts throughout the several figures.

Figure 1:
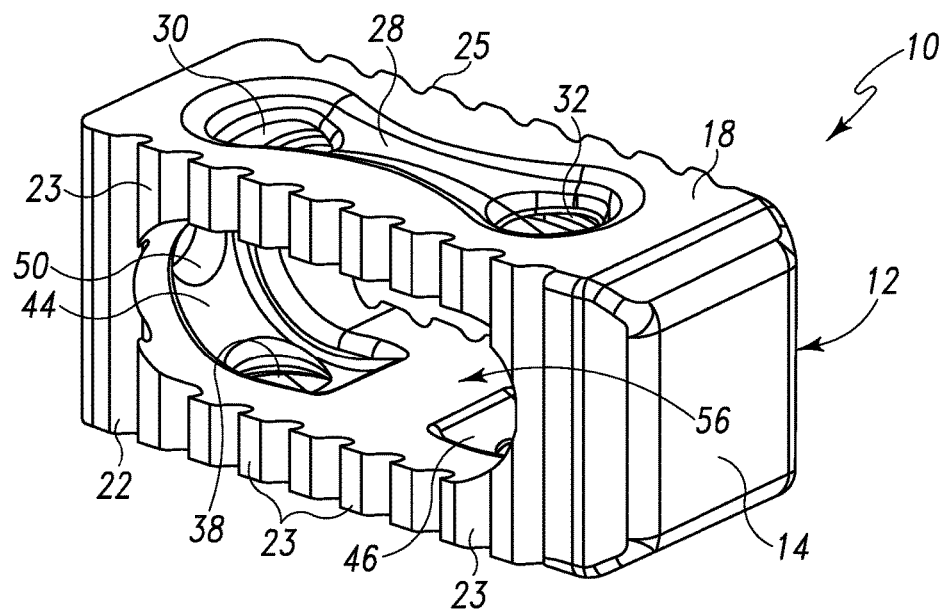
FIG. 1 is an anterior perspective view of a lumbar interbody device fashioned in accordance with the present principles.
Figure 2:
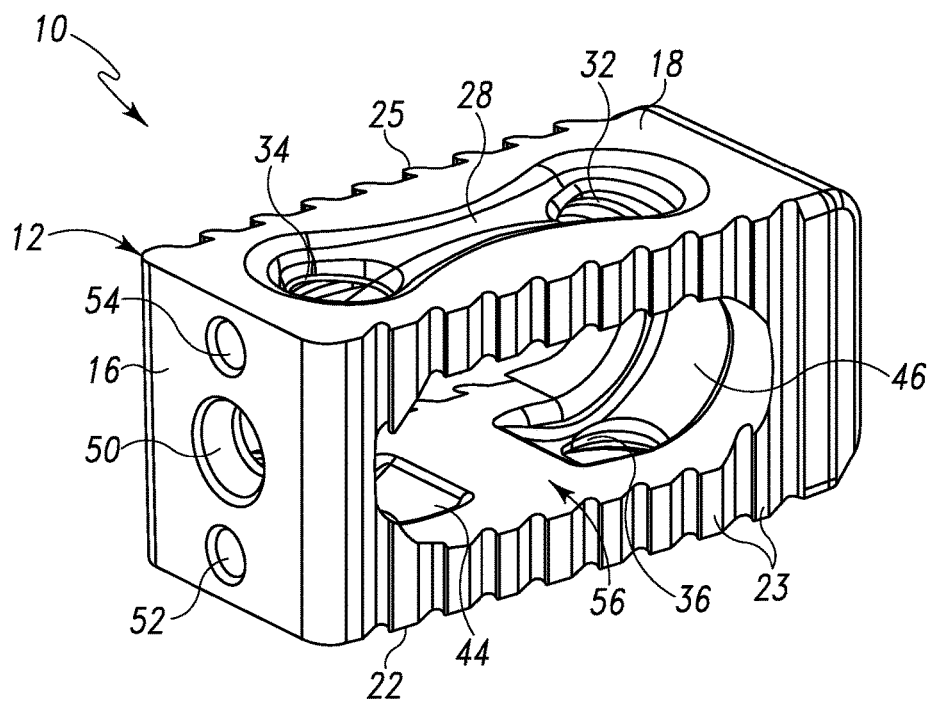
FIG. 2 is a posterior perspective view of the lumbar interbody device of FIG. 1.
Figure 3:
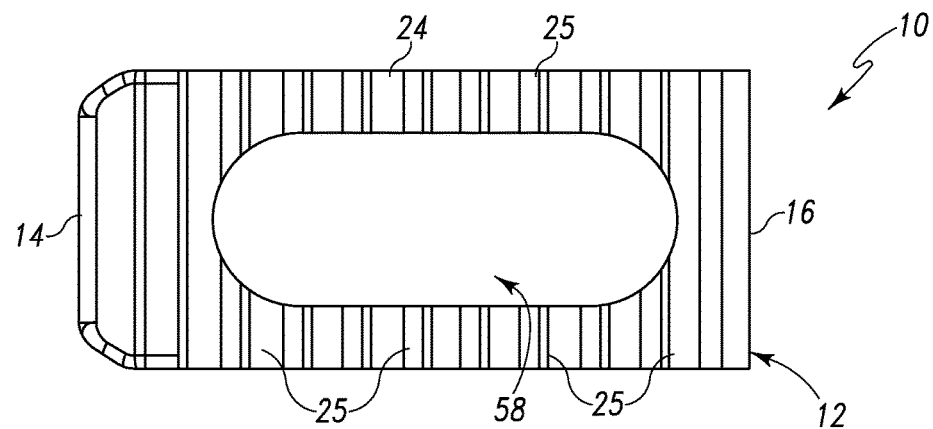
FIG. 3 is a superior plan view of the lumbar interbody device of FIG. 1, the anterior thereof facing to the left.

Detail of the features, functions and/or configuration of the components depicted in the various figures will now be presented. It should be appreciated that not all of the features of the components of the figures may necessarily be described. Some of these non-discussed features as well as discussed features are inherent from the figures. Other non-discussed features may be inherent in component geometry and/or configuration.

DETAILED DESCRIPTION OF EMBODIMENTS

Referring to the Figures and in particular to FIGS. 1-6, there is depicted an exemplary interbody device, generally designated 10, fashioned in accordance with the present principles. The interbody device 10 is preferably, but not necessarily, used as a lumbar interbody device and is defined by a generally rectangular body 12. The body 12 is fabricated from a bio-compatible material such as stainless steel, titanium, a titanium alloy, composite, polymer or the like. The body 12 is sized to be received between adjacent vertebrae but to not extend beyond the periphery of the vertebra. As such, the body 12 may be fabricated in various sizes to accommodate various sizes of lumbar vertebrae. Moreover, the body 12 may be sized such that several interbody devices 10 may be situated as indicated above.

The body 12 has an anterior end 14 and a posterior end 16 each of which is essentially flat, a superior side 22 having a plurality of serrations or teeth 23, and an inferior side 24 having a plurality of serrations or teeth 25. It should be appreciated that since the body 12 is symmetrical, the superior side 22 may be the inferior side while the inferior side 24 may be the superior side, while maintaining the anterior end 14 and the posterior end 16. Therefore, the terms superior and inferior are arbitrary. The superior side 22 and the inferior side 24 are configured to abut the lower surface of an upper vertebra and the upper surface of a lower vertebra that is adjacent the upper vertebra, respectively. The body 12 also defines a first lateral side 18 and a second lateral side 20. Again, it should be appreciated that the nomenclature first and second is arbitrary and thus interchangeable.

The interior of the body 12 is essentially hollow or has a cavity therein that may be used to receive bone growth material and/or for allowing bony ingrowth therein. The interior cavity of the body 12 communicates with the exterior of the body 12 via various openings in the body 12. Particularly, the superior side 22 has a generally ovoid opening 56 and the inferior side 24 has a generally ovoid opening 58. The openings 56 and 58 are generally diametrically opposite one another. Moreover, the first lateral side 18 has a generally hourglass depression or concavity 28 having a first essentially pear-shaped bore 30 on one end of the depression 28 that is in communication with the interior of the body 12 and a second essentially pear-shaped bore 32 on the other end of the depression 28 that is in communication with the interior of the body 12. The second lateral side 20 has a generally hourglass depression or concavity 34 having a first essentially pear-shaped bore 36 on one end of the depression 34 that is in communication with the interior of the body 12 and a second essentially pear-shaped bore 38 on the other end of the depression 34 that is in communication with the interior of the body 12.

In accordance with an aspect of the present invention, the body 12 has a first undercut 44 on the interior of the body 12 that extends in an arc from the bore 30 of the first lateral side 18 to the bore 34 of the second lateral side 20 and a second undercut 46 on the interior of the body 12 that extends in an arc from the bore 32 of the first lateral side 18 to the bore 36 of the second lateral side 20. The arc of the first undercut 44 extends along the inner wall of the posterior end 16. The arc of the second undercut 46 extends along the inner wall of the anterior end 14.

Figure 4:
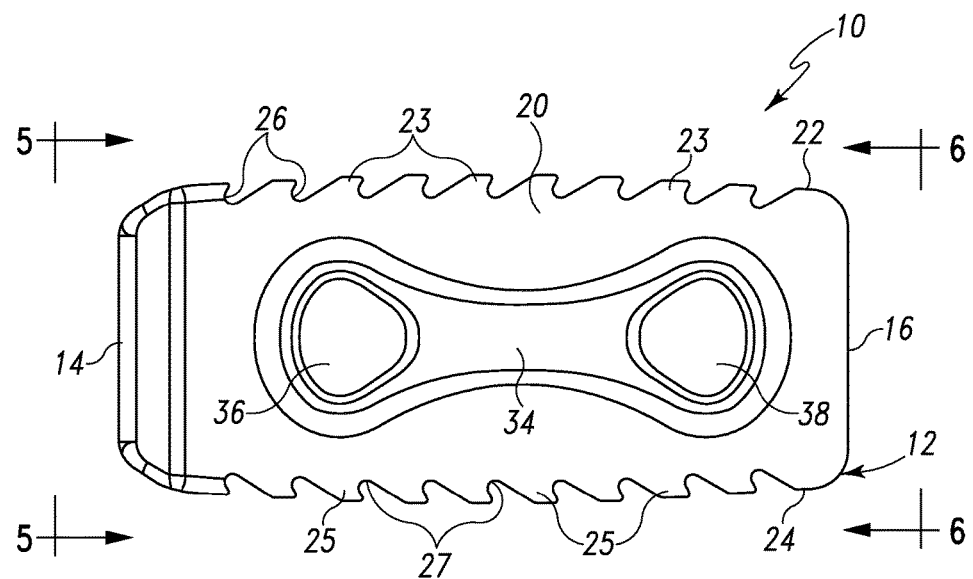
FIG. 4 is a side view of the lumbar interbody device of FIG. 1, the anterior thereof facing to the left.
Figure 5:
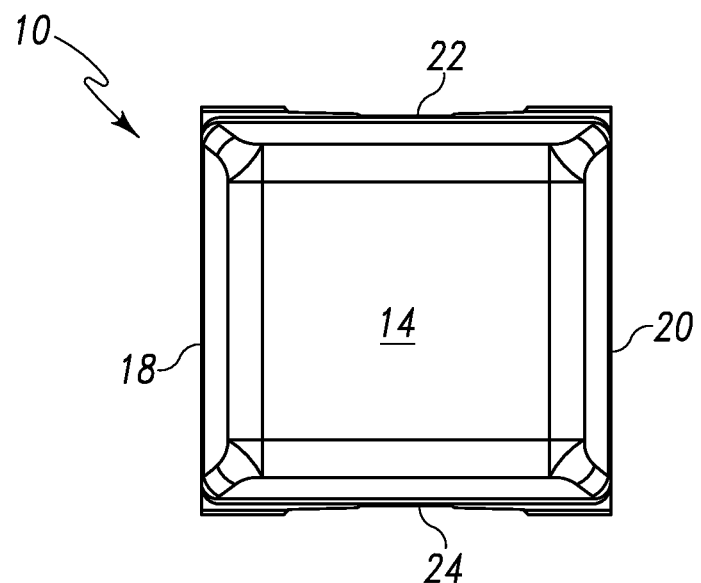
FIG. 5 is an anterior plan view of the lumbar interbody device of FIG. 1 taken along line 5-5 of FIG. 4.
Figure 6:
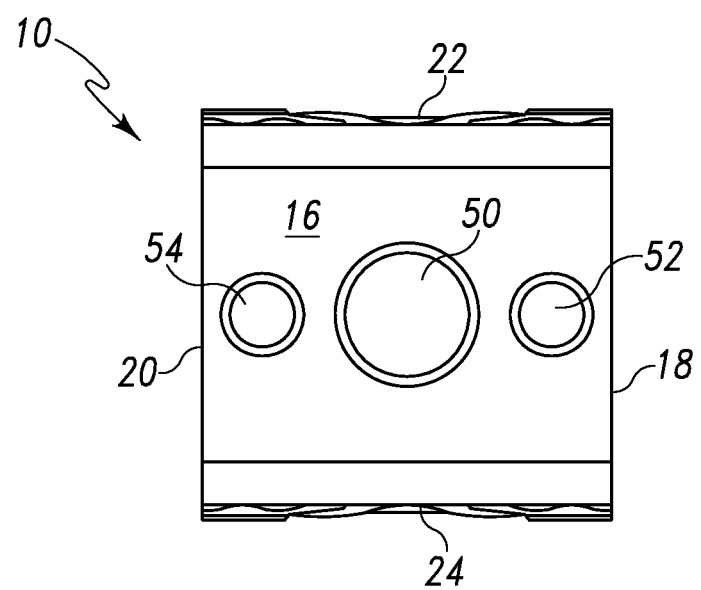
FIG. 6 is a posterior plan view of the lumbar interbody device of FIG. 1 taken along line 6-6 of FIG. 4.
Figure 7:
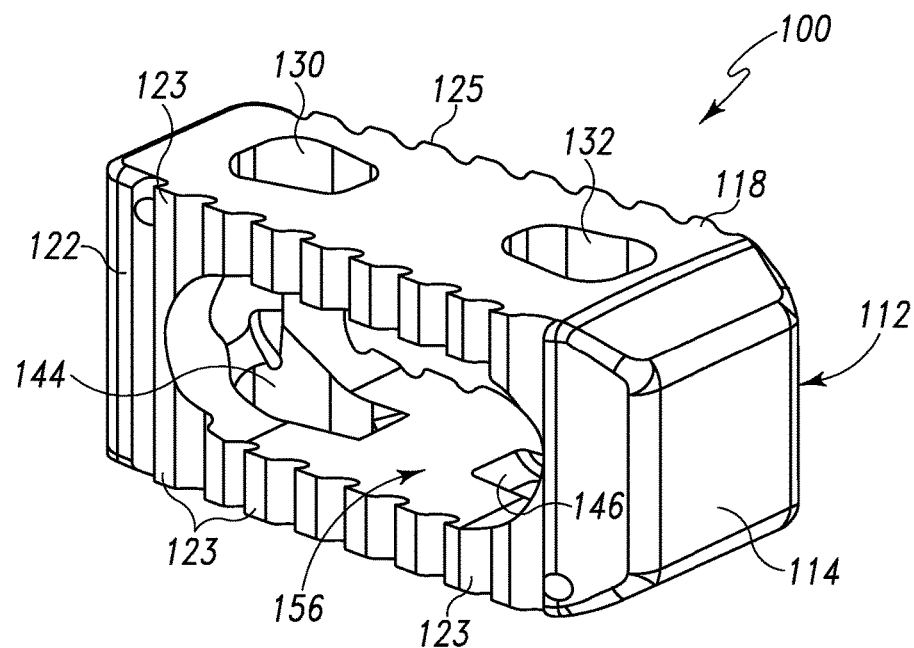
FIG. 7 is an anterior perspective view of a lumbar interbody device fashioned in accordance with the present principles.
Figure 8:
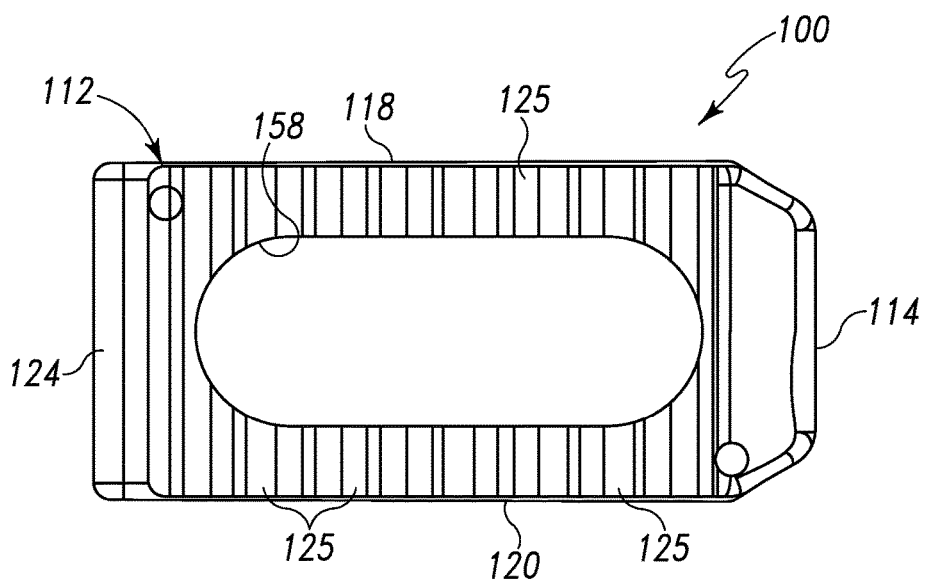
FIG. 8 is a superior plan view of the lumbar interbody device of FIG. 7, the anterior thereof facing to the right.
Figure 9:
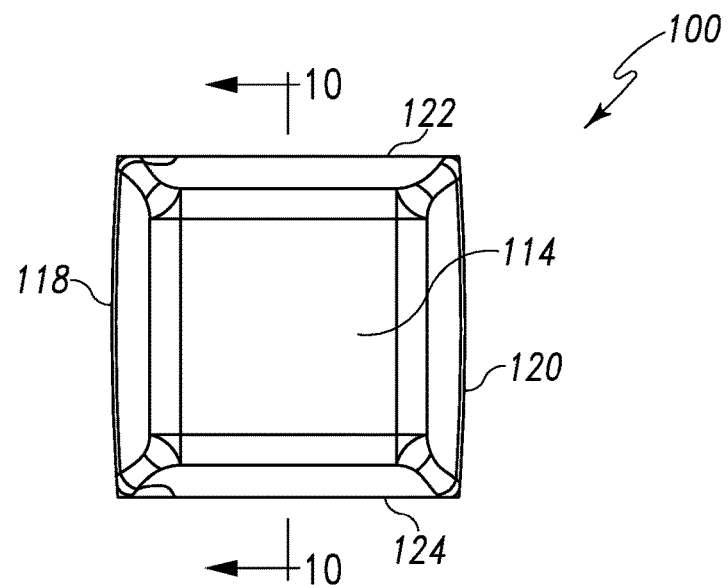
FIG. 9 is an anterior plan view of the lumbar interbody device of FIG. 7.

In accordance with another aspect of the present invention, the superior side 22 has a plurality of teeth or serrations 23 that extend from the first lateral side 18 to the second lateral side 20 and define pockets 27 therebetween. As best seen in FIG. 4, the teeth 23 project towards the posterior end 16 of the body 12. This allows the insertion of the interbody device 10 into a disc space (i.e. the space between adjacent vertebrae) in an anterior-first manner while preventing and/or inhibiting the interbody device 10 from backing out posteriorly. Likewise, the inferior side 24 has a plurality of teeth or serrations 25 that extend from the first lateral side 18 to the second lateral side 20 and define pockets 26 therebetween. As best seen in FIG. 4, the teeth 25 project towards the posterior end 16 of the body 12. This allows the insertion of the interbody device 10 into a disc space (i.e. the space between adjacent vertebrae) in an anterior-first manner while preventing and/or inhibiting the interbody device 10 from backing out posteriorly.

The posterior end 16 also includes a center or main bore 50 that provides communication between the exterior of the body 12 and the interior thereof. First and second side bores 52, 54 are also provided in the posterior end 16. These bores allow the use of a tool to insert the interbody device 10 into the disc space and/or the packing of bone growth material into the interior of the body 12.

Referring now to FIGS. 7-10, there is depicted another exemplary interbody device, generally designated 100, fashioned in accordance with the present principles. The interbody device 100 is preferably, but not necessarily, used as a lumbar interbody device and is defined by a generally rectangular body 112. The body 112 is fabricated from a bio-compatible material such as stainless steel, titanium, a titanium alloy, composite, polymer or the like. The body 112 is sized to be received between adjacent vertebrae but to not extend beyond the periphery of the vertebra. As such, the body 112 may be fabricated in various sizes to accommodate various sizes of lumbar vertebrae. Moreover, the body 112 may be sized such that several interbody devices 100 may be situated as indicated above.

The body 112 has an anterior end 114 and a posterior end 116 each of which is shown as being flat. These ends, however, may be other than flat. For instance, the ends may be formed as an aggressive bullet shape. The body 112 also has a superior side 122 having a plurality of serrations or teeth 123 and an inferior side 124 having a plurality of serrations or teeth 125. It should be appreciated that since the body 112 is symmetrical about a longitudinal axis thereof, the superior side 122 may be the inferior side while the inferior side 124 may be the superior side, while maintaining the anterior end 114 and the posterior end 116. Therefore, the terms superior and inferior are arbitrary. The superior side 122 and the inferior side 124 are configured to abut the lower surface of an upper vertebra and the upper surface of a lower vertebra that is adjacent the upper vertebra, respectively. The body 112 also defines a first lateral side 118 and a second lateral side 120. Again, it should be appreciated that the nomenclature first and second is arbitrary and thus interchangeable.

The interior of the body 112 is essentially hollow or has a cavity therein that may be used to receive bone growth material and/or for allowing bony ingrowth therein. The interior cavity of the body 112 communicates with the exterior of the body 112 via various openings in the body 112. Particularly, the superior side 122 has a generally ovoid opening 156 and the inferior side 124 has a generally ovoid opening 158. The openings 156 and 158 are generally diametrically opposite one another. Moreover, the first lateral side 118 has a first essentially pear-shaped bore 130 that is in communication with the interior of the body 112 and a second essentially pear-shaped bore 132 that is in communication with the interior of the body 112. While not discernable in the figures, the second lateral side 120 has a first essentially pear-shaped bore that is in communication with the interior of the body 112 and a second essentially pear-shaped bore that is in communication with the interior of the body 112.

In accordance with an aspect of the present invention, the body 112 has ingrowth undercuts in the interior of the body 112. These undercuts aid in retaining the interbody device in its positioned placement once bony ingrowth occurs. Particularly, the body 112 has a first undercut 159 on the interior of the body 112 that extends in an arc from the bore 130 of the first lateral side 118 to the bore (not shown) of the second lateral side 120 and a second undercut 161 on the interior of the body 112 that extends in an arc from the bore 132 of the first lateral side 118 to the bore (not shown) of the second lateral side 120. The arc of the first undercut 156 extends along the inner wall of the posterior end 116. The arc of the second undercut 161 extends along the inner wall of the anterior end 114.

Figure 10:
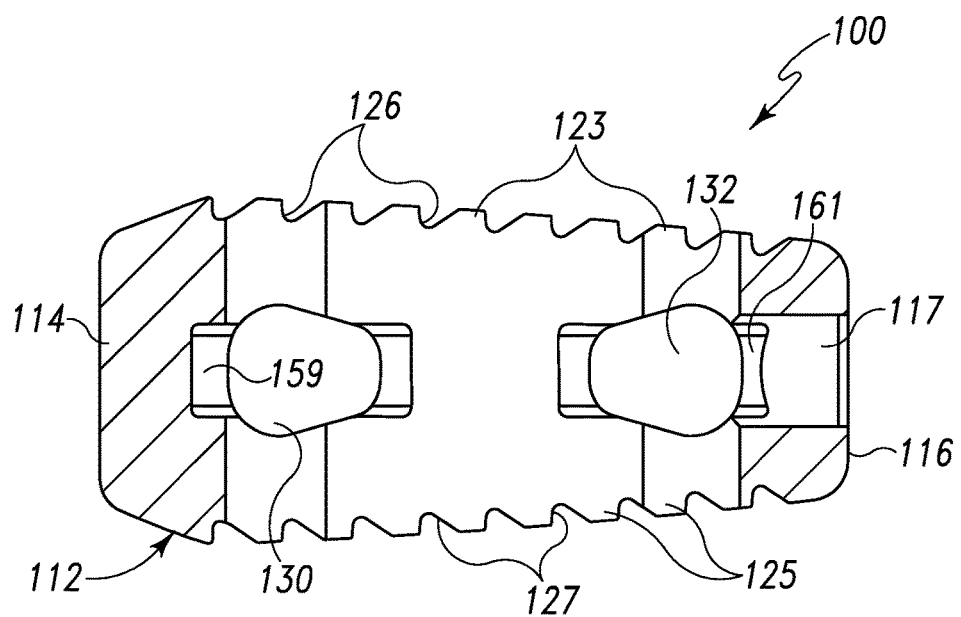
FIG. 10 is a sectional view of the lumbar interbody device of FIG. 7 taken along line 10-10 of FIG. 9.
Figure 11:
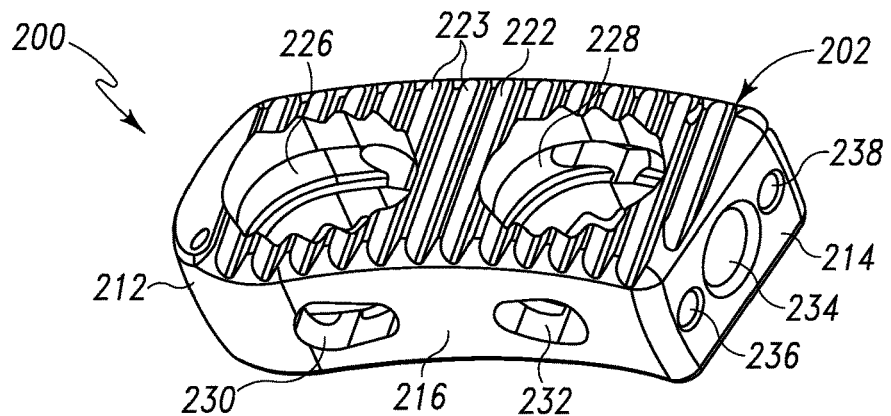
FIG. 11 is a posterior perspective view of a lumbar interbody device fashioned in accordance with the present principles.

In accordance with another aspect of the present invention, the superior side 122 has a plurality of teeth or serrations 123 that extend from the first lateral side 118 to the second lateral side 120 and define pockets 126 therebetween. As best seen in FIG. 10, the teeth 126 project towards the posterior end 116 of the body 112. This allows the insertion of the interbody device 100 into a disc space (i.e. the space between adjacent vertebrae) in an anterior-first manner while preventing and/or inhibiting the interbody device 100 from backing out posteriorly. Likewise, the inferior side 124 has a plurality of teeth or serrations 125 that extend from the first lateral side 118 to the second lateral side 120 and define pockets 127 therebetween. As best seen in FIG. 10, the teeth 125 project towards the posterior end 116 of the body 112. This allows the insertion of the interbody device 100 into a disc space (i.e. the space between adjacent vertebrae) in an anterior-first manner while preventing and/or inhibiting the interbody device 100 from backing out posteriorly.

Moreover, as best seen in FIG. 10, the superior side 122 and the inferior side 124 are not parallel or essentially parallel as are the superior and inferior sides of the interbody device 10. Rather, the superior and inferior sides 122, 124 are tapered inwardly towards each other from the posterior end 116 to the anterior end 114. This structure provides a significant increase in strength to the loading of the interbody device.

The posterior end 116 also includes a center or main bore 117 that provides communication between the exterior of the body 112 and the interior thereof. This bore allows the use of a tool to insert the interbody device 100 into the disc space and/or the packing of bone growth material into the interior of the body 112.

Referring now to FIGS. 11-15, there is depicted another exemplary interbody device, generally designated 200, fashioned in accordance with the present principles. The interbody device 200 is preferably, but not necessarily, used as a lumbar interbody device and is defined by a generally arc-shaped body 202. The body 202 is fabricated from a bio-compatible material such as stainless steel, titanium, a titanium alloy, composite, polymer or the like. The body 202 is sized to be received between adjacent vertebrae but to not extend beyond the periphery of the vertebra. As such, the body 202 may be fabricated in various sizes to accommodate various sizes of lumbar vertebrae. Moreover, the body 202 may be sized such that several interbody devices 200 may be situated as indicated above. The body 202 is sized to be received between adjacent vertebrae but to not extend beyond the periphery of the vertebra. As such, the body 202 may be fabricated in various sizes to accommodate various sizes of lumbar vertebrae. Moreover, the body 202 may be sized such that several interbody devices 200 may be situated as indicated above.

The body 202 has an anterior end 214 and a posterior end 216, the anterior end of which is arced and the posterior end 216 of which is rounded. The body 202 also has a superior side 222 having a plurality of serrations or teeth 223 and an inferior side 224 having a plurality of serrations or teeth 225. The superior side 222 and the inferior side 224 are configured to abut the lower surface of an upper vertebra and the upper surface of a lower vertebra that is adjacent the upper vertebra, respectively. The body 202 also defines a first lateral side 216 and a second lateral side 218. Again, it should be appreciated that the nomenclature first and second is arbitrary and thus interchangeable.

The body 202 has a first and second hollow or cavity therein that may be used to receive bone growth material and/or for allowing bony ingrowth therein. The first and second cavities communicate with the exterior of the body 202 via various openings in the body 202. Particularly, the superior side 222 has a first generally oval opening 226 and a second general oval opening 228. The inferior side 224 has a first generally oval opening (not seen) and a second generally oval opening (not seen). The oval openings are generally diametrically opposite one another. Moreover, the first lateral side 216 has a first essentially pear-shaped bore 230 that is in communication with the first cavity of the body 202 and a second essentially pear-shaped bore 232 that is in communication with the second cavity of the body 202. While not discernable in the figures, the second lateral side 218 has a first essentially pear-shaped bore (not seen) that is in communication with the second cavity of the body 202 and a second essentially pear-shaped bore (not seen) that is in communication with the second cavity of the body 202.

In accordance with an aspect of the present invention, the body 202 has ingrowth undercuts in the interior of the body 202. These undercuts aid in retaining the interbody device in its positioned placement once bony ingrowth occurs. Particularly, the body 202 has a first undercut 226 in the first cavity of the body 202 that extends in an arc and a second undercut 228 in the second cavity of the body 202 that extends in an arc. The arc of the first undercut 226 extends along the inner wall of the anterior end 214, while the arc of the second undercut 228 extends along the inner wall of the posterior end 216.

Figure 15:
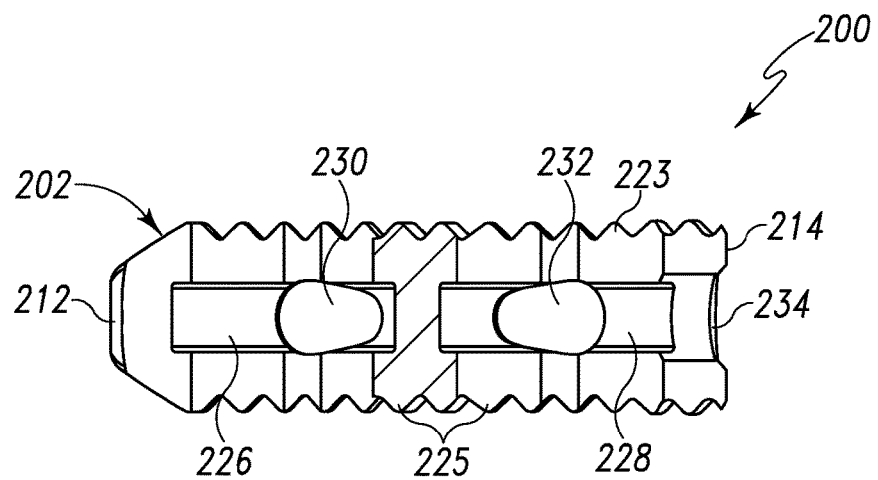
FIG. 15 is a sectional view of the lumbar interbody device of FIG. 11 taken along line 15-15 of FIG. 12.
Figure 16:
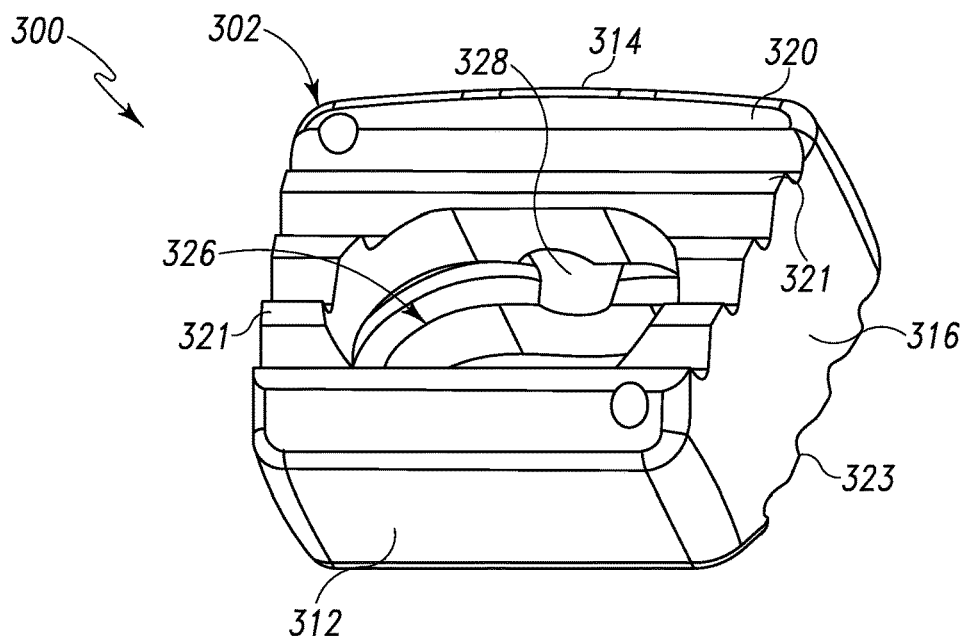
FIG. 16 is an anterior perspective view of a cervical interbody device fashioned in accordance with the present principles.
Figure 17:
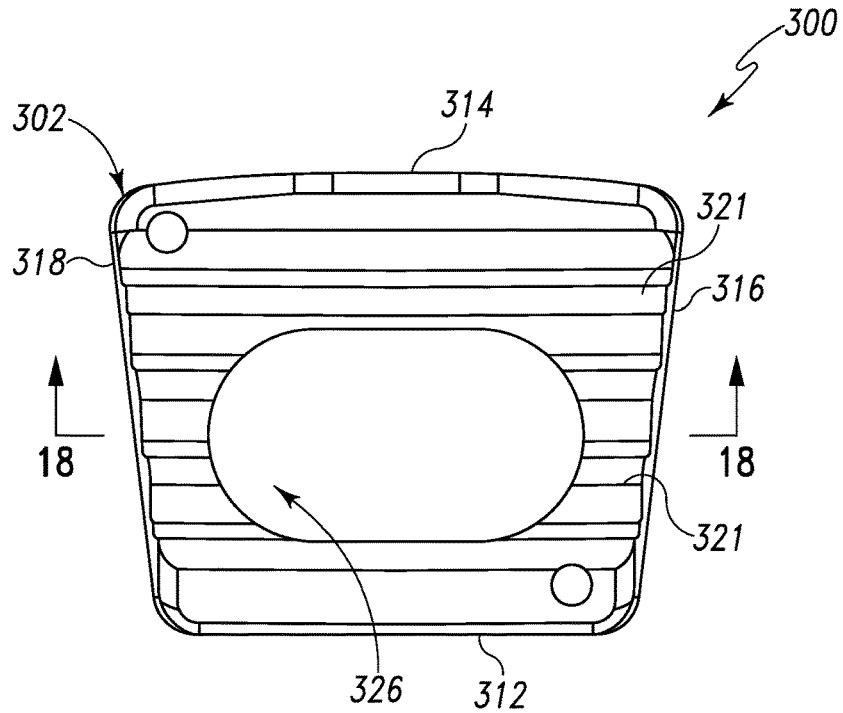
FIG. 17 is a superior plan view of the cervical interbody device of FIG. 16.
Figure 18:
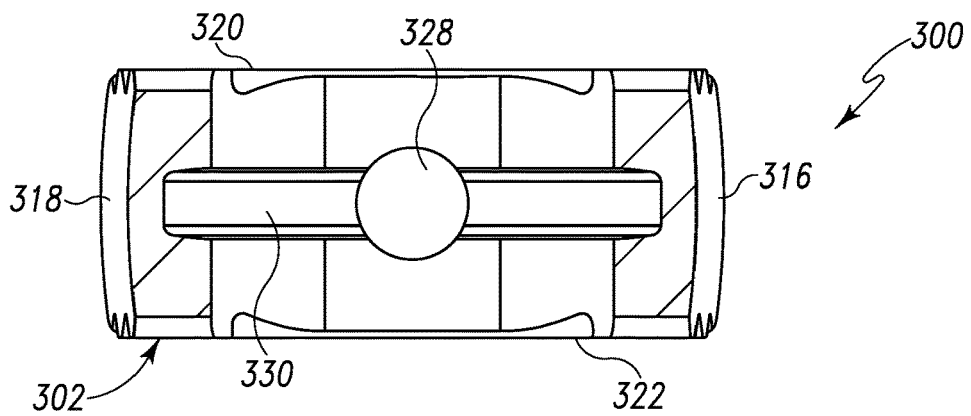
FIG. 18 is a sectional view of the cervical interbody device of FIG. 16 taken along line 18-18 of FIG. 17.

In accordance with another aspect of the present invention, the superior side 222 has a plurality of teeth or serrations 223 that extend from the first lateral side 216 to the second lateral side 218, while the inferior side 224 has a plurality of teeth or serrations 225 that extend from the first lateral side 216 to the second lateral side 218. As best seen in FIG. 15, the teeth 223 and 225 project upwards from the body 202 and are generally evenly spaced.

Figure 12:
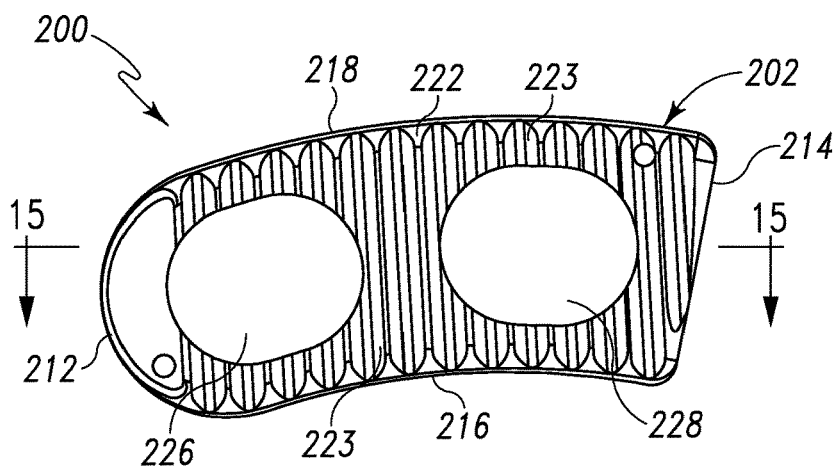
FIG. 12 is a superior plan view of the lumbar interbody device of FIG. 11, the posterior thereof facing to the right.
Figure 13:
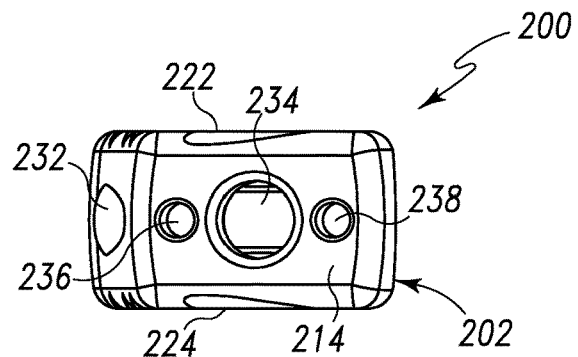
FIG. 13 is a posterior plan view of the lumbar interbody device of FIG. 11.
Figure 14:
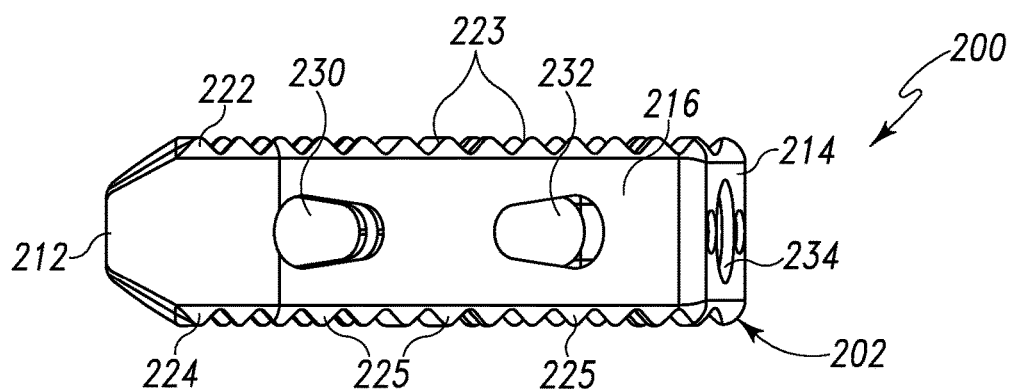
FIG. 14 is a side view of the lumbar interbody device of FIG. 11.

Moreover, as best seen in FIG. 12, first and second lateral sides 216, 218 are curved. This bowing provides a significant increase in strength to the loading of the part.

The posterior end 214 also includes a center or main bore 234 and first and second side bores 236 and 238 are also provided in the posterior end 16. These bores allow the use of a tool to insert the interbody device 200 into the disc space.

Referring now to FIGS. 16-19, there is depicted another exemplary interbody device, generally designated 300, fashioned in accordance with the present principles. The interbody device 300 is preferably, but not necessarily, used as a cervical interbody device and is defined by a generally trapezoidal body 302. The body 302 is fabricated from a bio-compatible material such as stainless steel, titanium, a titanium alloy, composite, polymer or the like. The body 302 is sized to be received between adjacent vertebrae but to not extend beyond the periphery of the vertebra. As such, the body 302 may be fabricated in various sizes to accommodate various sizes of cervical vertebrae.

The body 302 has an anterior end 312 and a posterior end 314, the anterior end 312 being essentially flat while the posterior end 314 is slightly curved. The body 302 also has a superior side 320 and an inferior side 322. It should be appreciated that since the body 302 is symmetrical about a longitudinal axis, the superior side may be the inferior side while the inferior side may be the superior side, while maintaining the anterior end 312 and the posterior end 314. Therefore, the terms superior and inferior are arbitrary. The superior side 320 and the inferior side 322 are configured to abut the lower surface of an upper vertebra and the upper surface of a lower vertebra that is adjacent the upper vertebra, respectively. The body 302 also defines a first lateral side 316 and a second lateral side 308. Again, it should be appreciated that the nomenclature first and second is arbitrary and thus interchangeable.

The interior of the body 302 is essentially hollow or has a cavity therein that may be used to receive bone growth material and/or for allowing bony ingrowth therein. The interior cavity of the body 302 communicates with the exterior of the body 302 via various openings in the body 302. Particularly, the superior side 320 has a generally ovoid opening 326 and the inferior side 322 has a generally ovoid opening (not seen) in like manner to the ovoid opening 326. The openings are generally diametrically opposite one another.

Figure 19:
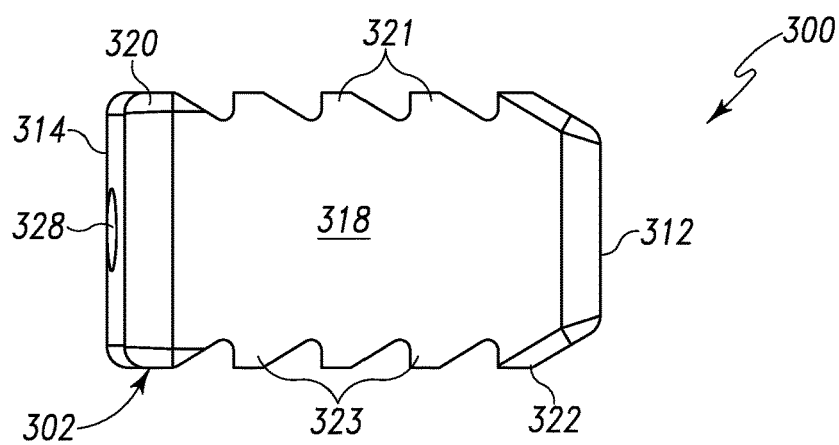
FIG. 19 is a side view of the cervical interbody device of FIG. 16, the anterior thereof facing to the right.

In accordance with an aspect of the present invention, the body 302 has ingrowth undercuts in the interior of the body 302. These undercuts aid in retaining the interbody device in its positioned placement once bony ingrowth occurs. Particularly, the body 302 has an undercut 330 in the interior of the body 302 that extends in an arc. In accordance with another aspect of the present invention, the superior side 320 has a plurality of teeth or serrations 321 that extend from the first lateral side 318 to the second lateral side 320 and define pockets therebetween. As best seen in FIG. 19, the teeth 321 project towards the posterior end 314 of the body 302. This allows the insertion of the interbody device 300 into a disc space (i.e. the space between adjacent vertebrae) in an anterior-first manner while preventing and/or inhibiting the interbody device 300 from backing out posteriorly. Likewise, the inferior side 322 has a plurality of teeth or serrations 323 that extend from the first lateral side 318 to the second lateral side 320 and define pockets therebetween. As best seen in FIG. 19, the teeth 323 project towards the posterior end 314 of the body 302. This allows the insertion of the interbody device 300 into a disc space (i.e. the space between adjacent vertebrae) in an anterior-first manner while preventing and/or inhibiting the interbody device 300 from backing out posteriorly.

The posterior end 314 also includes a center or main bore 328 that provides communication between the exterior of the body 302 and the interior thereof. This bore allows the use of a tool to insert the interbody device 302 into the disc space and/or the packing of bone growth material into the interior of the body 302.

Also, it should be appreciated that since the anterior end 312 is smaller in length than the posterior end 314, the first and second lateral sides 316 and 318 are not parallel to one another. This provides a significant increase in strength to the loading of the part.

Figure 20:
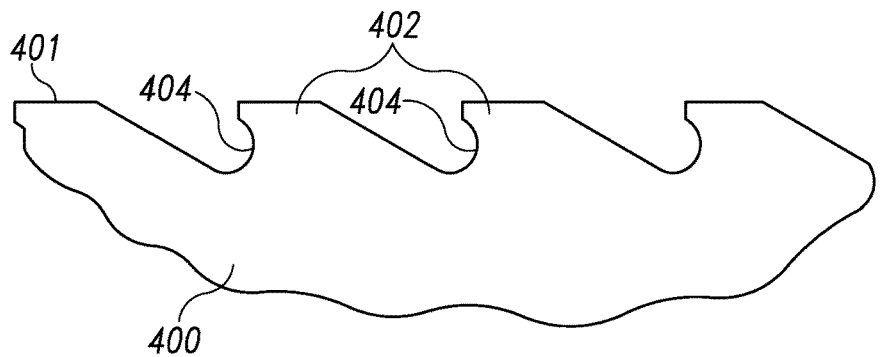
FIG. 20 is an enlarged fragmentary view of an alternative serration or tooth design applicable to all of the present interbody devices.
Figure 21:
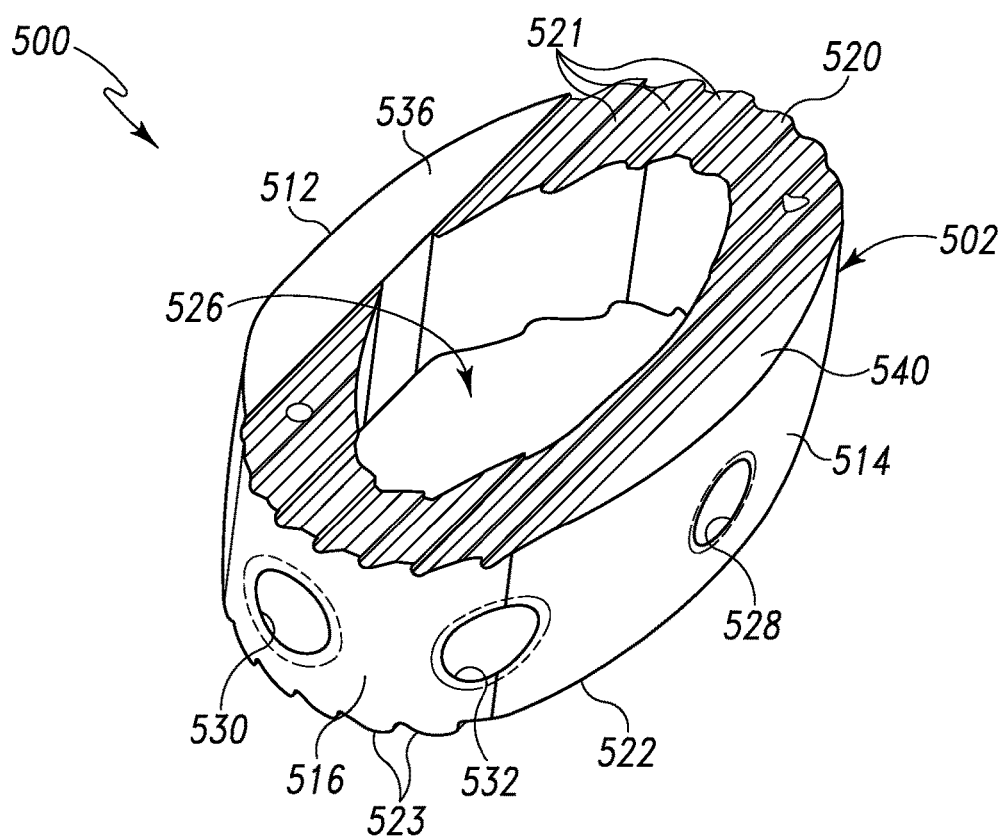
FIG. 21 is a side perspective view of a cement restrictor/interbody device fashioned in accordance with the present principles.
Figure 22:
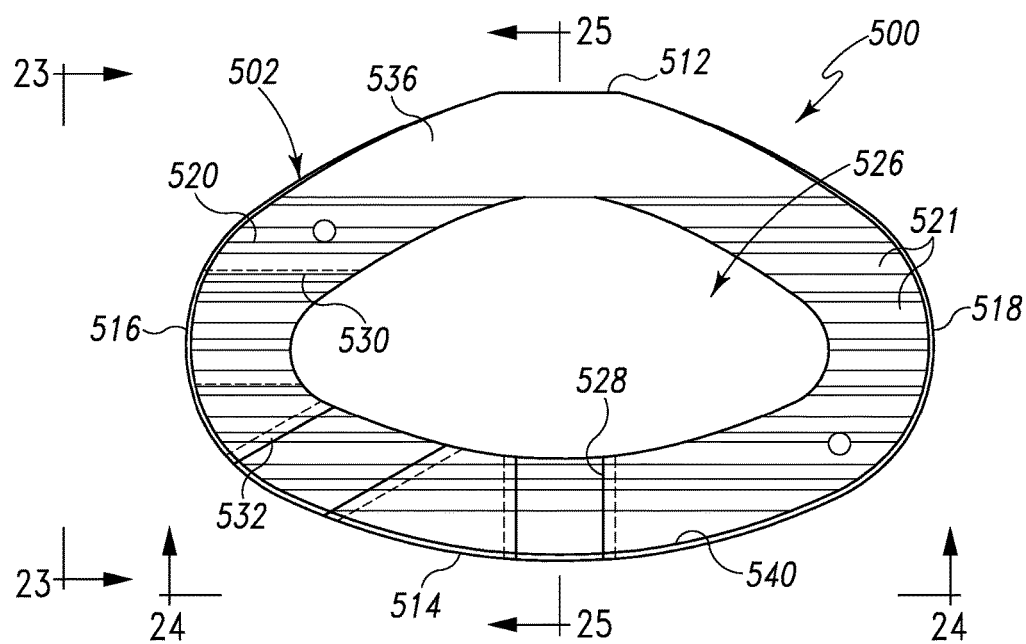
FIG. 22 is a top plan view of the device of FIG. 21.
Figure 23:
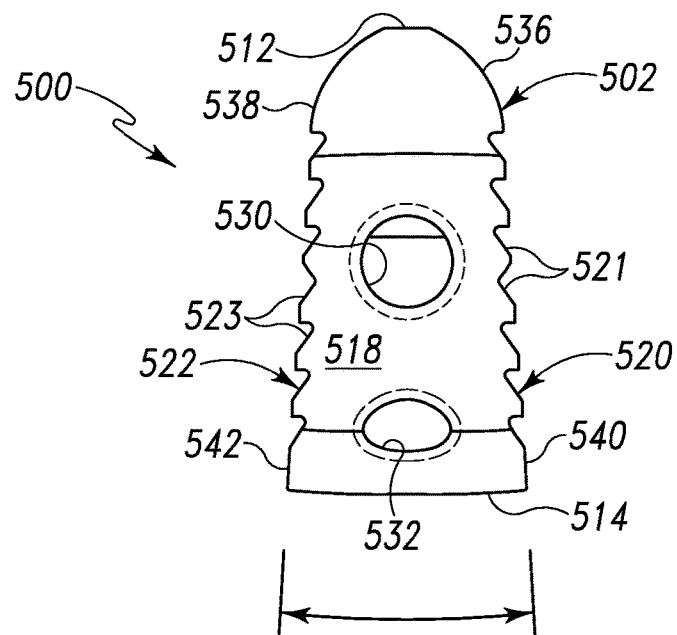
FIG. 23 is a left side view of the device of FIG. 21 as viewed from the top plan view of FIG. 22.
Figure 24:
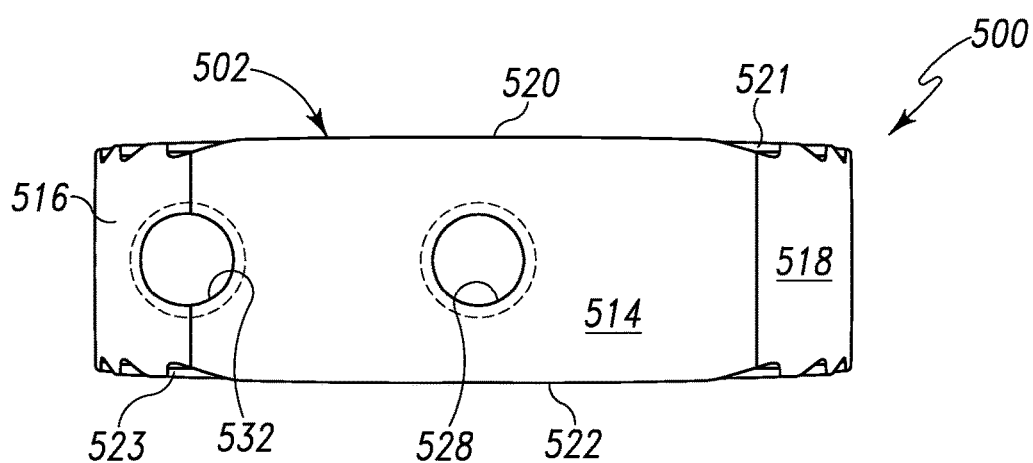
FIG. 24 is a bottom view of the device of FIG. 21 as viewed from the top plan view of FIG. 22.
Figure 25:
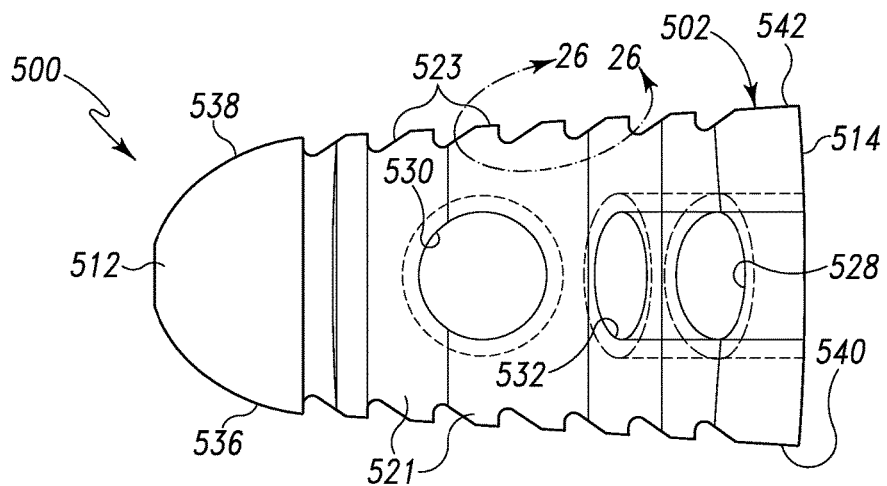
FIG. 25 is a sectional view of the device of FIG. 21 taken along line 25-25 of FIG. 22.

FIG. 20 depicts a fragmentary view of an alternative embodiment of serrations or teeth applicable to the various interbody devices described herein. Particularly, an interbody device body 400 includes teeth or serrations 402 on an inferior and superior surface 401 that face toward the posterior of the interbody device. The teeth 402 define rounded undercuts 404 therein.

Referring now to FIGS. 21-26, there is depicted another exemplary interbody device, generally designated 500, fashioned in accordance with the present principles. The interbody device 500 may be used as a cervical or lumbar interbody device and is defined by a generally ovoid body 502. The body 502 is fabricated from a bio-compatible material such as stainless steel, titanium, a titanium alloy, composite, polymer or the like. The body 502 is sized to be received between adjacent vertebrae but to not extend beyond the periphery of the vertebra. As such, the body 502 may be fabricated in various sizes to accommodate various sizes of cervical vertebrae. This is represented in FIGS. 27A, 27B, 28A, and 28B.

Figure 27A:
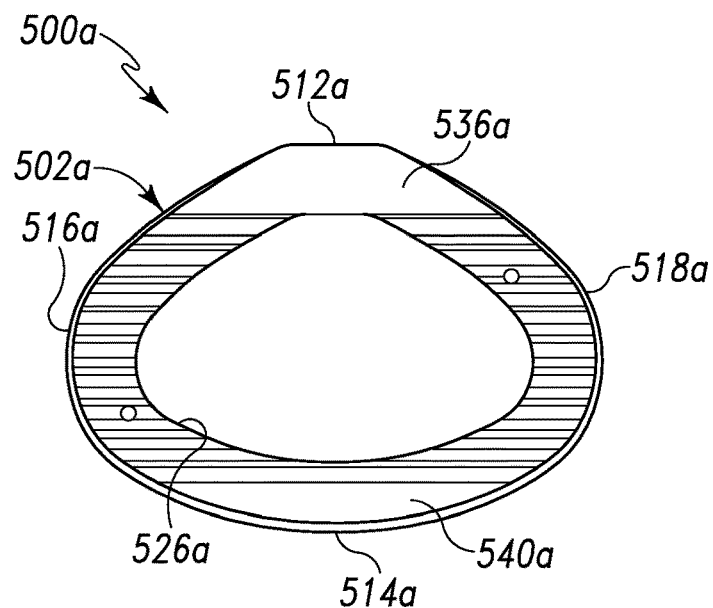
FIGS. 27A and 27B are is a combined top plan view and right side view, respectively, thereof of one size of the device of FIG. 21.
Figure 27B:
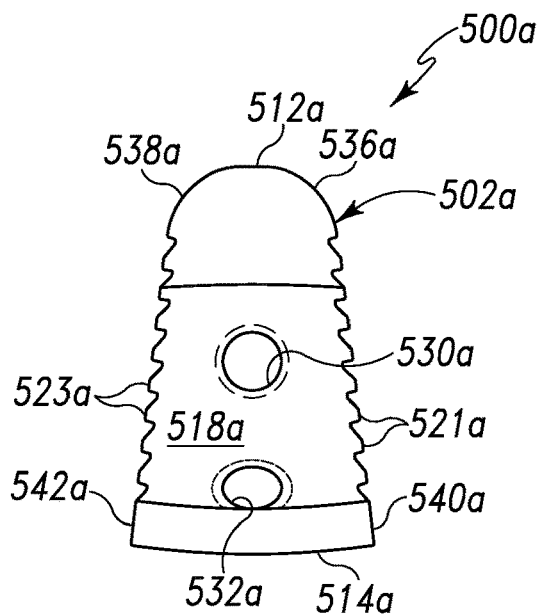
Figure 28A:
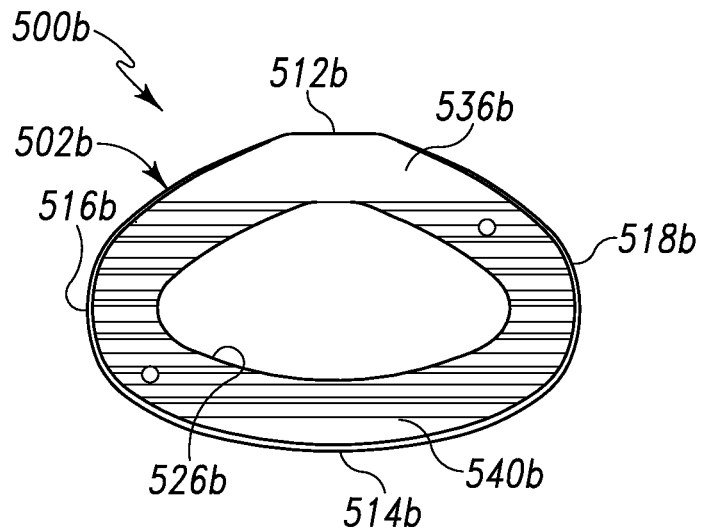
FIGS. 28A and 28B are is a combined top plan view and right side view, respectively, thereof of one size of the device of FIG. 21.
Figure 28B:
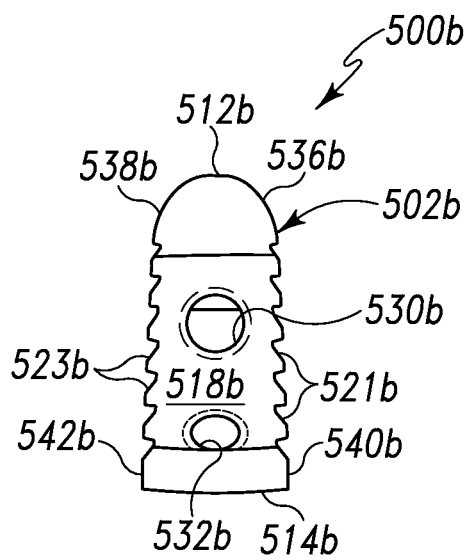

Particularly, FIGS. 27A and 27B depict one size of the interbody device 500 designated 500a having the same configuration as the interbody device 500 but with the letter designation "a" after corresponding numerical parts thereof. FIG. 27A shows a top plan view of the interbody device 500a on the left side of the figure, and a right side view of the interbody device 500a relative to the top plan view on the right side of the figure. FIGS. 28A and 28B depict another size of the interbody device 500 designated 500b having the same configuration as the interbody device 500 but with the letter designation "b" after corresponding numerical parts thereof. FIG. 28A shows a top plan view of the interbody device 500b on the left side of the figure, and a right side view of the interbody device 500b relative to the top plan view on the right side of the figure.

Referring back to FIGS. 21-26, the body 502 has an anterior end 512 and a posterior end 514, the anterior end 512 being essentially curved but truncated (flat) at the peak thereof, with the posterior end 514 being also curved. The body 502 also has a superior side 520 and an inferior side 522. It should be appreciated that since the body 502 is symmetrical about a longitudinal axis, the superior side may be the inferior side while the inferior side may be the superior side, while maintaining the anterior end 512 and the posterior end 514. Therefore, the terms superior and inferior are arbitrary.

The superior side 520 and the inferior side 522 are configured to abut the lower surface of an upper vertebra and the upper surface of a lower vertebra that is adjacent the upper vertebra, respectively. The body 502 also defines a first lateral side 516 and a second lateral side 518. Again, it should be appreciated that the nomenclature first and second is arbitrary and thus interchangeable.

The interior of the body 502 is essentially hollow or has a cavity 526 therein that may be used to receive bone growth material and/or for allowing bony ingrowth therein. The interior cavity 526 of the body 502 communicates with the exterior of the body 502 via other various openings in the body 502.

Particularly, the posterior end 514 has a bore 528 that extends from the exterior of the body 502 to the cavity 526. The first lateral side 516 has a bore 530 that extends from the exterior of the body 502 to the cavity 516. A bore 532 is situated at the transition between the posterior end 514 and the first lateral side 516 that likewise extends from the exterior of the body 502 to the cavity 516.

In accordance with an aspect of the present invention, the superior side 520 has a plurality of teeth or serrations 521 that extend from the first lateral side 516 to the second lateral side 518, but between a flat 540 on the superior side 520 proximate the posterior end 514 to a taper 536 on the superior side 520 proximate the anterior end 512. The teeth 521 project towards the posterior end 514 of the body 502. This allows the insertion of the interbody device 500 into a disc space (i.e. the space between adjacent vertebrae) in an anterior-first manner while preventing and/or inhibiting the interbody device 500 from backing out posteriorly. Likewise, the inferior side 522 has a plurality of teeth or serrations 523 that extend from the first lateral side 516 to the second lateral side 518, but between a flat 542 on the inferior side 522 proximate the posterior end 514 to a taper 538 on the inferior side 522 proximate the anterior end 512. The teeth 523 project towards the posterior end 514 of the body 502. This allows the insertion of the interbody device 500 into a disc space (i.e. the space between adjacent vertebrae) in an anterior-first manner while preventing and/ or inhibiting the interbody device 500 from backing out posteriorly.

Figure 26:
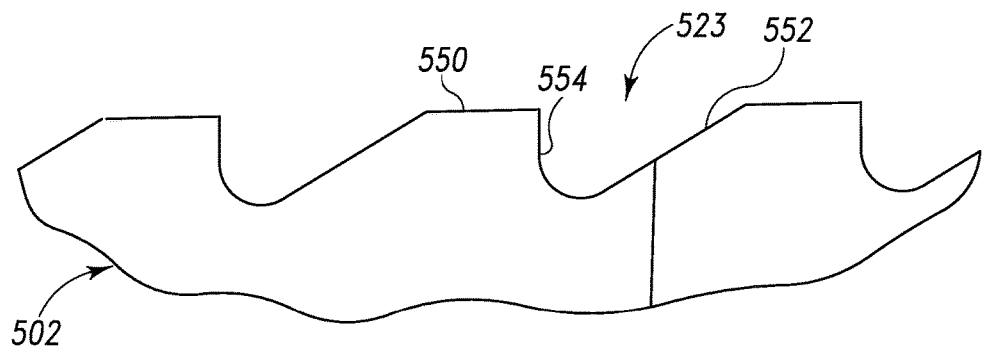
FIG. 26 is an enlarged view of a portion of the sectional view of the device of FIG. 25 taken along line 26-26 thereof.

FIG. 26 depicts a fragmentary view of the serrations or teeth 523 of the interbody device 500. The teeth or serrations 523 define rounded troughs 554 between flats 550 and tapers 552. The teeth or serrations 523 face toward the posterior of the interbody device.

While the invention has been illustrated and described in detail in the drawings and foregoing description, the same is to be considered as illustrative and not restrictive in character, it being understood that only preferred embodiments have been shown and described and that all changes and modifications that come within the spirit of the invention are desired to be protected.

What is claimed is:

1. An implant comprising:
   a body having a first outer surface with a first depression;
   a cavity formed within the body and at least partially defined by an interior surface of the body;
   a first groove formed in and at least partially extending along the interior surface;
   a first bore extending through the body having a first bore end opening into and located within the first depression and a second bore end opening into and located within the first groove.

2. The implant of claim 1, further comprising a second outer surface on the body, and a second bore extending through the body between, and in communication with, the first groove and the second outer surface.

3. An implant comprising:
   a body having a first outer surface and a second outer surface, wherein the first outer surface comprises a first depression, wherein the second outer surface comprises a second depression;
   a cavity formed within the body and at least partially defined by an interior surface of the body;
   a first groove formed in and at least partially extending along the interior surface;
   a first bore extending through the body having a first end within the first depression and a second end within the first groove;
   a second bore extending through the body between, and in communication with, the first groove and the second outer surface, wherein the second bore passes through the second depression and into the first groove.

4. The implant of claim 3, further comprising:
   a second groove formed in the interior surface of the cavity, wherein the second groove partially extends on the interior surface of the body and is spaced apart from the first groove;

a third bore extending between, and in communication with, the first depression in the first outer surface, the first groove and the cavity;

a fourth bore extending between, and in communication with, the second depression in the second outer surface, the second groove and the cavity.

5. The implant of claim 3, wherein the first depression includes a first enlarged end and a second enlarged end.

6. The implant of claim 5, wherein the second depression includes a first enlarged end and a second enlarged end.

7. The implant of claim 1, wherein the implant is one of a lumbar, cervical and long bone implant.

8. The implant of claim 1, wherein the body is one of rectangular, tapered, arcuate, trapezoidal, oval.

9. An implant comprising:
a body having a first outer surface with a first depression;
a cavity formed within the body and at least partially defined by an interior surface of the body;
a first groove formed in and at least partially extending along the interior surface;
a first bore extending through the body having a first end within the first depression and a second end within the first groove;
a second outer surface spaced apart from the first outer surface;
a third outer surface extending between the first and second outer surfaces; and
wherein the third outer surface includes a first opening in communication with the cavity.

10. The implant of claim 9, further comprising a fourth outer surface extending between the first and second outer surfaces and spaced apart from the third outer surface, wherein the fourth outer surface includes a second opening in communication with the cavity.

11. The implant of claim 10, further comprising first serrations on the third outer surface and second serrations on the fourth outer surface, the first and second serrations configured to allow implantation but inhibit backing out of the body, wherein the first and second serrations each project towards a common direction of the body.

12. The implant of claim 10, further comprising:
a second cavity formed within the body;
a third opening formed in the third outer surface and in communication with the second cavity; and
a fourth opening formed in the fourth outer surface and in communication with the second cavity.

13. An implant comprising:
a body having a first outer surface, a second outer surface, and an interior surface, the first outer surface having a first depression;

a cavity within the body and at least partially defined by the interior surface of the body;
a first groove extending along the interior surface of the body;
a first bore extending through the body and having a first open end in the first depression and a second open end in the first groove;
a second groove distinct from the first groove and extending along the interior surface of the body;
a second bore extending through the body and having a first open end in the first depression and a second open end in the second groove;
a third bore extending through the body between, and in communication with, the first groove and the second outer surface.

14. The implant of claim 13, wherein the second outer surface comprises a second depression, wherein the third bore passes through the second depression and into the first groove.

15. The implant of claim 13, further comprising a fourth bore extending between, and in communication with, the second depression in the second outer surface, the second groove and the cavity.

16. The implant of claim 13, wherein the first depression includes a first enlarged end and a second enlarged end.

17. An implant comprising:
a trapezoidal body having a first side and a second side spaced apart from the first side, the trapezoidal body also having a first outer surface, a second outer surface, a third outer surface between the first and second outer surfaces, and a fourth outer surface between the first and second outer surfaces, wherein the first, second, third, and fourth outer surfaces extend between the first side and the second side;
a depression formed in the first outer surface of the trapezoidal body;
a cavity formed within and at least partially defined by an interior surface of the trapezoidal body;
a groove formed in and extending along the interior surface of the trapezoidal body;
a bore extending through the trapezoidal body and into the first depression and into the first groove;
first serrations disposed on the first side and second serrations on the second side, wherein the first and second serrations each project towards a common direction of the trapezoidal body.

18. The implant of claim 17, wherein the first outer surface is curved and defining a first dimension, and the second outer surface is generally flat and defining a second dimension less than the first dimension.

* * * * *